(12) United States Patent
McCombie et al.

(10) Patent No.: US 10,004,409 B2
(45) Date of Patent: Jun. 26, 2018

(54) SYSTEM FOR CALIBRATING A BLOOD PRESSURE MEASUREMENT BASED ON VASCULAR TRANSIT OF A PULSE WAVE

(71) Applicant: SOTERA WIRELESS, INC., San Diego, CA (US)

(72) Inventors: Devin McCombie, San Diego, CA (US); Guanqun Zhang, San Diego, CA (US)

(73) Assignee: SOTERA WIRELESS, INC., San Diego, CA (US)

( * ) Notice: Subject to any disclaimer, the term of this patent is extended or adjusted under 35 U.S.C. 154(b) by 70 days.

(21) Appl. No.: 14/833,078

(22) Filed: Aug. 22, 2015

(65) Prior Publication Data

US 2016/0143546 A1 May 26, 2016

Related U.S. Application Data

(60) Provisional application No. 62/040,958, filed on Aug. 22, 2014.

(51) Int. Cl.
*A61B 5/021* (2006.01)
*A61B 5/0205* (2006.01)
(Continued)

(52) U.S. Cl.
CPC ........ *A61B 5/02125* (2013.01); *A61B 5/0205* (2013.01); *A61B 5/026* (2013.01); *A61B 5/02028* (2013.01); *A61B 5/02233* (2013.01); *A61B 5/0402* (2013.01); *A61B 5/11* (2013.01); *A61B 5/7225* (2013.01);
(Continued)

(58) Field of Classification Search
CPC ............ A61B 5/02125; A61B 5/02028; A61B 5/0205; A61B 5/02233; A61B 5/0402; A61B 5/026; A61B 5/11; A61B 5/7225; A61B 5/7228; A61B 2560/0223; A61B 2562/0219
See application file for complete search history.

(56) References Cited

U.S. PATENT DOCUMENTS

2003/0036685 A1 2/2003 Goodman
2004/0030261 A1 2/2004 Rantala
(Continued)

OTHER PUBLICATIONS

International Search Report and Written Opinion issued in PCT/US2015/046436 dated Dec. 31, 2015.

*Primary Examiner* — Catherine Voorhees
(74) *Attorney, Agent, or Firm* — Acuity Law Group, PC; Michael A. Whittaker (57) ABSTRACT

The invention provides a system and method for measuring vital signs (e.g. SYS, DIA, SpO2, heart rate, and respiratory rate) and motion (e.g. activity level, posture, degree of motion, and arm height) from a patient. The system features: first and second sensors configured to independently generate time-dependent waveforms indicative of one or more contractile properties of the patient's heart; and a cuff-based oscillometric module. A processing component, typically worn on the patient's body and featuring a microprocessor, receives the time-dependent waveforms generated by the different sensors and processes them to determine patient-specific calibration values for use in a continuous blood pressure measurement based on pulse wave velocity (PWV).

6 Claims, 3 Drawing Sheets

(51) Int. Cl.
    *A61B 5/11*     (2006.01)
    *A61B 5/02*     (2006.01)
    *A61B 5/022*     (2006.01)
    *A61B 5/026*     (2006.01)
    *A61B 5/00*     (2006.01)
    *A61B 5/0402*     (2006.01)
    *A61B 5/024*     (2006.01)
    *A61B 5/0404*     (2006.01)

(52) U.S. Cl.
    CPC ........ *A61B 5/7278* (2013.01); *A61B 5/02225* (2013.01); *A61B 5/02416* (2013.01); *A61B 5/0404* (2013.01); *A61B 2560/0223* (2013.01); *A61B 2562/0219* (2013.01)

(56) References Cited

U.S. PATENT DOCUMENTS

| | | | |
|---|---|---|---|
| 2009/0018422 A1* | 1/2009 | Banet | A61B 5/02007 600/324 |
| 2009/0076398 A1 | 3/2009 | Li et al. | |
| 2010/0241011 A1 | 9/2010 | McCombie et al. | |
| 2011/0152699 A1 | 6/2011 | Cho | |
| 2012/0108933 A1* | 5/2012 | Liang | A61B 5/0002 600/365 |
| 2012/0215117 A1* | 8/2012 | Karst | A61B 5/02125 600/486 |
| 2012/0283583 A1 | 11/2012 | Batkin et al. | |
| 2013/0184595 A1 | 7/2013 | Mukkamala et al. | |
| 2014/0155767 A1 | 6/2014 | Fukuda et al. | |

* cited by examiner

SYSTEM FOR CALIBRATING A BLOOD PRESSURE MEASUREMENT BASED ON VASCULAR TRANSIT OF A PULSE WAVE

The present application claims priority to U.S. Provisional Application 62/040,958 filed Aug. 22, 2014, which is hereby incorporated in its entirety including all tables, figures, and claims.

BACKGROUND OF THE INVENTION

Non-invasive measurement of blood pressure (BP) using cuff-based methods provides adequate data for many applications in medicine. However, cuff-based methods have some disadvantages that limit their utility in certain clinical situations. For example, as cuff-based methods are by definition a discontinuous measurement of blood pressure, in BP that occur between measurements are missed. Additionally, the inflation of the cuff may disturb the patient and the consequences of these disturbances are alterations of the BP and undesired arousal of the patient during sleep.

An alternative approach relates to a continuous, non-invasive and indirect measurement of BP based on the vascular transit of a pulse pressure wave. A number of variables been described in the art as relating, at least in general terms, to arterial blood pressure. In one example, pulse transit time (PTT) is defined as the time for a pressure wave launched by contraction of the left ventricle of the heart into a patient's arterial system to travel between two arterial sites. PTT may be considered to be a function of arterial compliance (or "stiffness"), the propagation distance of the pressure pulse being measured, and arterial blood pressure, and has been shown in a number of studies to correlate to systolic (SYS), diastolic (DIA), and mean (MAP) blood pressure. Similarly, pulse wave velocity (PWV) is a measure of the velocity at which the same pressure wave moves between two arterial sites. PWV is often described as a direct measure of arterial compliance, but is also a function of vessel dimension and arterial blood pressure.

Travel of a pulse pressure wave through a portion of the vasculature may be measured with a vital signs monitor that includes separate modules to determine both an electrocardiogram (ECG) and pulse oximetry (SpO2). During a measurement, multiple electrodes typically attach to a patient's chest to determine a time-dependent ECG component characterized by a sharp spike called the 'QRS complex'. The QRS complex indicates an initial depolarization of ventricles within the heart and, informally, marks the beginning of the heartbeat and a pressure pulse that follows. SpO2 is typically measured using a sensor that attaches to a patient's finger, and includes optical systems operating in both the red and infrared spectral regions. A photodetector measures radiation emitted from the optical systems that transmits through the patient's finger (although other body sites, e.g., the ear, forehead, and nose, can also be used in place of the finger).

During a measurement, a microprocessor analyses both red and infrared radiation detected by the photodetector to determine the patient's blood oxygen saturation level and a time-dependent waveform called a photoplethysmograph ('PPG'). Time-dependent features of the PPG indicate both pulse rate and a volumetric absorbance change in an underlying artery caused by the propagating pressure pulse. A number of publications describe the relationship between PTT and blood pressure. For example, U.S. Pat. Nos. 5,316,008; 5,857,975; 5,865,755; and 5,649,543 each describe an apparatus that includes conventional sensors that measure an ECG and PPG, which are then processed to determine PTT. Gesche et al., Eur. J. Appl. Physiol. 112: 309-15, 2012, discloses a similar apparatus for relating PWV to systolic blood pressure. Each of these publications is hereby incorporated by reference in its entirety.

To account for patient-dependent properties, such as arterial compliance, pulse pressure wave-based measurements of blood pressure are typically 'calibrated' using a conventional blood pressure cuff. Typically during the calibration process the blood pressure cuff is applied to the patient, used to make one or more blood pressure measurements, and then left on the patient. Going forward, the calibration blood pressure measurements are used, along with a change in PTT or PWV to determine the patient's blood pressure and blood pressure variability.

SUMMARY OF THE INVENTION

This invention provides a method and system for calibrating a body-worn vital sign monitor configured to determine a continuous noninvasive blood pressure measurement using pulse pressure wave data. The system features a series of sensors that measure time-dependent PPG, ECG, and cuff-based pressure waveforms. Following an initial calibration, arterial blood pressure is typically calculated from the PPG and ECG waveforms.

Once determined, blood pressure and other vital signs can be further processed, typically with a server within a hospital, to alert a medical professional if the patient begins to decompensate. Processing the combination of the patient's motion and vital sign information is particularly useful, as these components are integrally related: a patient that is walking, for example, may have an accelerated heart rate and is likely breathing; the system can thus be designed to not alarm on these parameters, even if they exceed predetermined, preprogrammed levels.

In a first aspect, the present invention provides a body-worn vital sign monitoring system. The system includes a first sensor that generates a first time-dependent waveform indicative of one or more contractile properties of the patient's heart. In certain embodiments this is provided as an optical sensor, typically worn on the patient's finger, which includes a light source that emits radiation and a photodetector that detects radiation after it irradiates a portion of the patient's body to generate a time-dependent PPG. The system further includes a second sensor that generates a second time-dependent waveform indicative of one or more contractile properties of the patient's heart. In certain embodiments this is provided as an electrical sensor featuring at least two electrodes that measure electrical signals from the patient's body, and an electrical circuit that receives the electrical signals and processes them to determine a time-dependent ECG.

The system additionally includes a pneumatic system featuring an inflatable cuff, a pump, and a pressure sensor that, collectively, make an oscillometric blood pressure measurement. During a calibration measurement, the inflatable cuff attaches to the patient's arm and is inflated by the pump. The pressure sensor measures a time-dependent pressure waveform representing a pressure within the inflatable cuff. Pulsations in the patient's arm caused by their blood pressure are superimposed on the pressure waveform.

The system further comprises a processing component which is configured to receive the first and second time-dependent waveforms indicative of one or more contractile properties of the patient's heart and the time-dependent pressure waveform. The processing is further configured to analyze this set of waveforms to determine a calibration which accounts for patient-dependent properties, such as arterial compliance, in pulse pressure wave-based cNIBP measurements.

The processing component determines a time difference between ventricular depolarization occurring in a cardiac cycle, and arrival of a pressure wave at the first point resulting from blood flow caused by the ventricular depolarization through a vascular path of length ($L_t$). The inflatable cuff is configured to cover a portion of the vascular path of length ($L_c$), and transmit to the processing component a waveform indicative of cuff pressure on the patient's extremity during inflation. The processing component calculates a series of PAT as a function of cuff pressure during inflation of the inflatable cuff to above the patient's systolic blood pressure, wherein the inflation causes a compliance change in the vascular path of length $L_c$, thereby causing the PAT measured by the sensor device to lengthen as cuff pressure is increased. PAT is equal to the sum of PTT and the pre-ejection period (PEP). See, e.g., Zhang et al., J. Appl. Physiol. 111: 1681-86, 2011, which is hereby incorporated by reference in its entirety.

In related aspects, the present invention relates to methods determining patient-specific calibration values for use in a continuous blood pressure measurement based on pulse wave velocity (PWV) using the systems described herein. These methods comprise:

positioning on the patient
(i) a sensor device on a patient, the sensor device configured to measure sensor data indicative of pulse arrival time (PAT) at a first point on an extremity of the patient, the PAT defined as a time difference between ventricular depolarization occurring in a cardiac cycle, and arrival of a pressure wave at the first point resulting from blood flow caused by the ventricular depolarization through a vascular path of length ($L_t$), wherein the sensor device is operably connected to a processing component, and
(ii) an inflatable cuff device on the patient's extremity at a second point on the extremity of the patient at a position on the vascular path between the heart and the first point, the inflatable cuff device comprising an inflatable cuff which is configured to cover a portion of the vascular path of length ($L_c$) and an inflation pump, the inflatable cuff device configured to measure a waveform indicative of cuff pressure on the patient's extremity during inflation, wherein the inflatable cuff device is operably connected to the processing component;

receiving at the processing component the sensor data and the waveform indicative of cuff pressure, and causing the processing component to calculate therefrom a series of pulse arrival times ("PATs") as a function of cuff pressure during inflation of the inflatable cuff to above the patient's systolic blood pressure, wherein the inflation causes a compliance change in the vascular path of length $L_c$, thereby causing the PAT measured by the sensor device to lengthen as cuff pressure is increased; and determining using the processing component one or more coefficients which relate PWV to mean arterial pressure (MAP) by modeling the series of PATs measured as a function of cuff pressure as a nonlinear relationship.

The processing component then calculates one or more coefficients which relate PWV to mean arterial pressure (MAP) by modeling the series of PATs measured as a function of cuff pressure as a nonlinear relationship. In certain embodiments, the nonlinear relationship is a nonlinear regression function or a nonlinear least squares function. In a preferred embodiment, the nonlinear relationship is expressed as $$PAT(t) = \left(\frac{L_t - L_c}{aMAP_{cal} + pwv_0}\right) + \left(\frac{L_c}{a(MAP_{cal} - P_{cuff}(t)) + pwv_0}\right)$$

wherein $pwv_0$ is the PWV through the portion of the vascular path covered by the inflatable cuff, and a is a constant.

In certain embodiments, the processing component can determine a baseline pulse arrival time ($PAT_{cal}$) from the first and second time-dependent waveforms indicative of one or more contractile properties of the patient's heart obtained in the absence of pressure being applied by the inflatable cuff device, and a systolic pressure ($SYS_{cal}$), diastolic pressure ($DIA_{cal}$), and mean arterial pressure ($MAP_{cal}$) from the waveform indicative of cuff pressure on the patient's extremity obtained during inflation.

Using this information, the processing system can determine a linear (or non-linear) regression equation between systolic pressure and mean arterial pressure at the time of calibration and a linear (or non-linear) regression equation between diastolic pressure and mean arterial pressure at the time of calibration. A preferred embodiment of such a regression equation is $$DIA_{cal} = R_{dia} * MAP_{cal} + B_{dia}$$

In some instances where the intercept $B_{dia}$ is negligible, the ratio $R_{sys}$ and $R_{dia}$ are determined according to the equations $$R_{sys} = \left(\frac{SYS_{cal}}{MAP_{cal}}\right)$$

and $$R_{dia} = \left(\frac{DIA_{cal}}{MAP_{cal}}\right).$$

Subsequent to determining the one or more coefficients which relate PWV to MAP, in certain embodiments the processing component may be configured to determine a mean arterial pressure at a time t (MAP(t)) according to the equation $$MAP(t) = K \cdot \left(\frac{1}{PAT(t)} - \frac{1}{PAT_{cal}}\right) + MAP_{cal}$$

wherein K is $L_t/a$.

Subsequent to determining the one or more coefficients which relate PWV to MAP, in certain embodiments the processing component may also be configured to determine a systolic arterial pressure at a time t (SYS(t)) and a diastolic arterial pressure at a time t (DIA(t)) according to the equations $$SYS(t) = R_{sys} \cdot MAP(t) + B_{sys}$$

and $$DIA(t) = R_{dia} \cdot MAP(t) + B_{dia}$$

In those embodiments in which the first sensor is an optical sensor, such a sensor preferably features a source of electromagnetic radiation configured to irradiate tissue of the patient, and a detector configured to detect one or more properties of the electromagnetic radiation after it irradiates the tissue. This sensor can detect, for example, an optical waveform that is indicative of volumetric changes in the irradiated tissue caused by ventricular contraction of the patient's heart. More specifically, the optical waveform represents a time-dependent change in optical absorption of an underlying vessel resulting from the ejection of blood from the left ventricle. In those embodiments in which the second sensor is an electrical sensor, electrodes of the sensor are typically worn on the patient's chest in a conventional 'Einthoven's Triangle' configuration. The PAT may be determined as a time difference between a peak of a QRS complex of an ECG waveform and an inflection point in the optical waveform (corresponding, e.g., to a rising edge of the waveform).

In certain embodiments, the system and methods of the present invention further comprise determine the patient's motion, posture, and activity level. In these embodiments, the monitoring system can comprise, one, two, or preferably at least three motion-detecting sensors such as 3-axis accelerometers, each configured to be worn on a different location on the patient's body and each configured to generate at least one time-dependent ACC waveform. In preferred embodiments, one motion-detecting sensor is positioned on the chest, a second motion-detecting sensor is positioned on an upper arm, and a third motion-detecting sensor is positioned on the wrist of the same arm. When referring to the motion-detecting sensors, 'upper arm' means any portion of the arm above and including the elbow, e.g. the bicep, shoulder, and armpit. In the case of 3-axis accelerometers, each axis may be represented by a separate ACC waveform. The processing system is operably connected to receive the ACC waveform (s) generated by each motion-detecting sensor to determine at least one 'motion parameter' (e.g. the patient's posture, activity level, arm height, and degree of motion).

In certain embodiments, a wireless system operably connected to the processing system transmits the patient's blood pressure value (and optionally the motion parameter(s)) to a remote receiver. The remote receiver that receives information describing the patient's blood pressure values and optional motion data is typically configured to generate an alarm condition based on the blood pressure value, wherein the alarm condition can be modified based on a motion parameter. This remote receiver can comprise one or more of a server within a hospital or other care facility; a central display at a nursing station or other monitoring location which receives and displays the patient's blood pressure values and optional motion data for a plurality of patients; and a caregiver specific display such as a tablet computer, a cell phone, etc. which receives and displays the patient's blood pressure values and optional motion data for one or more patients for which the caregiver has responsibility.

The processing system of the present invention may involve one or more processors which may be located at a single location (e.g., in a body-worn format) or in multiple locations such that the processing is distributed across multiple pieces of hardware. The various sensors in the system may be communicated to the processing system in a number of wired and wireless configurations known in the art. In preferred embodiments one or more of the sensors are connected to the processing system using a bus system such as a controller area network (CAN) bus, the protocol (e.g. CANopen) of which permits the processing system to maintain tight temporal synchronization of the sensor signals transmitted to it, e.g., with a resolution of at least 250 msec, more preferably at least 100 msec, and more preferably still within 50 msec. By way of example, the data from one or more of the sensors may be transmitted in packet form with "time stamp" and "sensor source" data contained within the header of the packet so that the processing system can synchronize the data streams being received with the desired temporal resolution. This bus may operate in a wired and/or wireless configuration as desired by the artisan.

Still other embodiments are found in the following detailed description of the invention, and in the claims.

DETAILED DESCRIPTION OF THE INVENTION

System Overview

For purposes of the present application, the following abbreviations apply:

| | |
|---|---|
| cNIBP | An abbreviation for continuous non-invasive blood pressure |
| ECG | An abbreviation for the Electrocardiogram |
| PPG | An abbreviation for the Photoplethysmogram |
| PWV | An acronym for Pulse Wave Velocity. PWV is the speed at which a pressure pulse travels along an arterial pathway. |
| PAT | An acronym for Pulse Arrival Time. PAT is the time difference between the onset of the Infrared PPG signal and the peak of the ECG QRS complex for a single cardiac cycle. |
| VTT | An acronym for Vascular Transit Time. VTT is the time required by a pressure pulse to travel between two locations along an arterial pathway. |
| PEP | An acronym for Pre-ejection Period. PEP is the time difference between the opening of the aortic valve and the electrical activity of the heart. It consists of a period of electromechanical delay and a period of isovolumic contraction in the left ventricle. |
| $P_{tm}$ | An abbreviation for transmural pressure. $P_{tm}$ is the pressure acting across the arterial wall or the intra-arterial pressure minus the extra-arterial pressure. |
| $L_t$ | An abbreviation for the length of the arterial transit path between the aortic valve and the Princeps Pollicis artery at the base of the thumb |
| $MAP_{cal}$ | An abbreviation for the mean arterial pressure measured by the NIBP cuff |
| $PAT_{cal}$ | An abbreviation for the median pulse arrival time measured 30 seconds prior to the start of the NIBP cuff inflation |
| $SYS_{cal}$ | An abbreviation for the systolic arterial pressure measured by the NIBP cuff |
| $DIA_{cal}$ | An abbreviation for the diastolic arterial pressure measured by the NIBP cuff |
| $P_{cuff}$ | An abbreviation for the pressure in the NIBP cuff |
| $R_{sys}$ | An abbreviation for the ratio used by the cNIBP algorithm to calculate systolic pressure from MAP |
| $R_{dia}$ | An abbreviation for the ratio used by the cNIBP algorithm to calculate diastolic pressure from MAP |
| $P_{cuff}$ | An abbreviation for the pressure in the NIBP cuff |

Figure 1:
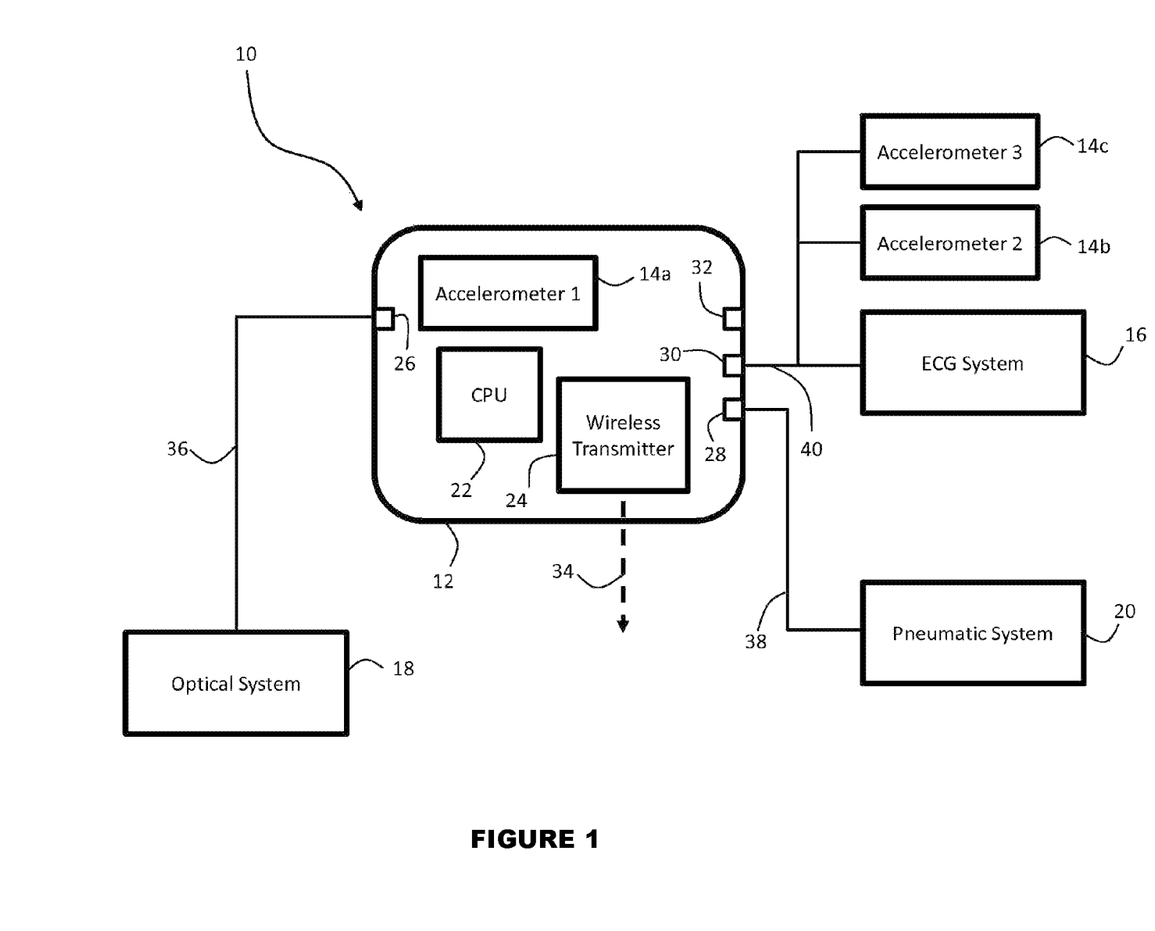
FIG. 1 depicts a schematic drawing of a body-worn vital sign monitor featuring three accelerometers for detecting motion, along with ECG, optical, and pneumatic systems for measuring vital signs.

FIG. 1 shows a schematic drawing of an exemplary body-worn vital sign monitor 10 according to the invention featuring a wrist-worn transceiver 12 that continuously determines vital signs (e.g. SYS, DIA, SpO2, heart rate, respiratory rate, and temperature) and motion (e.g. posture, arm height, activity level, and degree of motion) for, e.g., an ambulatory patient in a hospital. This body-worn vital sign monitor is described in detail in U.S. Pat. No. 8,672,854, which is hereby incorporated by reference.

A processing unit/transceiver 12 connects to three separate accelerometers 14a, 14b, 14c distributed along a patient's arm and torso and connected to a single cable. Each of these sensors measures three unique ACC waveforms, each corresponding to a separate axis (x, y, or z), which are digitized internally and sent to a computer processing unit (CPU) 22 within the transceiver 12 for processing. The transceiver 12 also connects to an ECG system 16 that measures an ECG waveform, an optical system 18 that measures a PPG waveform, and a pneumatic system 20 for making cuff-based 'indexing' blood pressure measurements according to the composite technique. Collectively, these systems 14a-c, 16, 18, and 20 continuously measure the patient's vital signs and motion.

The ECG 16 and pneumatic 20 systems are stand-alone systems that include a separate microprocessor and analog-to-digital converter. During a measurement, they connect to the transceiver 12 via cables 40 and 38 through connectors 28, 30 and supply digital inputs using a communication protocol that runs on a controller-area network (CAN) bus. The CAN bus is a serial interface, typically used in the automotive industry, which allows different electronic systems to effectively communicate with each other, even in the presence of electrically noisy environments. A third connector 32 also supports the CAN bus and is used for ancillary medical devices (e.g. a glucometer) that is either worn by the patient or present in their hospital room.

The optical system 18 features an LED and photodetector and, unlike the ECG 16 and pneumatic 20 systems, generates an analog electrical signal that connects through a cable 36 and connector 26 to the transceiver 12. As is described in detail below, the optical 18 and ECG 16 systems generate synchronized time-dependent waveforms that are processed with the composite technique to determine a PTT-based blood pressure along with motion information. The body-worn vital sign monitor 10 measures these parameters continuously and non-invasively characterize the hospitalized patient.

The first accelerometer 14a is surface-mounted on a printed circuited board within the transceiver 12, which is typically worn on the patient's wrist like a watch. The second 14b accelerometer is typically disposed on the upper portion of the patient's arm and attaches to a cable 40 that connects the ECG system 16 to the transceiver 12. The third accelerometer 14c is typically worn on the patient's chest proximal to the ECG system 16. The second 14b and third 14c accelerometers integrate with the ECG system 16 into a single cable 40, as is described in more detail below, which extends from the patient's wrist to their chest and supplies digitized signals over the CAN bus. In total, the cable 40 connects to the ECG system 16, two accelerometers 14b, 14c, and at least three ECG electrodes (shown in FIGS. 3A and 3B, and described in more detail below). The cable typically includes 5 separate wires bundled together with a single protective cladding: the wires supply power and ground to the ECG system 16 and accelerometers 14b, 14c, provide high signal and low signal transmission lines for data transmitted over the CAN protocol, and provide a grounded electrical shield for each of these four wires. It is held in place by the ECG electrodes, which are typically disposable and feature an adhesive backing, and a series of bandaid-like disposable adhesive strips. This simplifies application of the system and reduces the number of sensing components attached to the patient.

To determine posture, arm height, activity level, and degree of motion, the transceiver's CPU 22 processes signals from each accelerometer 14a-c with a series of algorithms, described in detail below. In total, the CPU can process nine unique, time-dependent signals ($ACC_{1-9}$) corresponding to the three axes measured by the three separate accelerometers. Specifically, the algorithms determine parameters such as the patient's posture (e.g., sitting, standing, walking, resting, convulsing, falling), the degree of motion, the specific orientation of the patient's arm and how this affects vital signs (particularly blood pressure), and whether or not time-dependent signals measured by the ECG 16, optical 18, or pneumatic 20 systems are corrupted by motion. Once this is complete, the processing unit/transceiver 12 uses an internal wireless transmitter 24 to send information in a series of packets, as indicated by arrow 34, to a central nursing station within a hospital. The wireless transmitter 24 typically operates on a protocol based on 802.11 and communicates with an existing network within the hospital. This information alerts a medical professional, such as a nurse or doctor, if the patient begins to decompensate. A server connected to the hospital network typically generates this alarm/alert once it receives the patient's vital signs, motion parameters, ECG, PPG, and ACC waveforms, and information describing their posture, and compares these parameters to preprogrammed threshold values.

The cuff within the cuff-based pneumatic system 20 is typically disposable and features an internal, airtight bladder that wraps around the patient's bicep to deliver a uniform pressure field. During the indexing measurement, pressure values are digitized by the internal analog-to-digital converter, and sent according to the CAN protocol, along with SYS, DIA, and MAP blood pressures, to the wrist-worn processing unit/transceiver 12 for processing as described above. Once the cuff-based measurement is complete, the cuff-based module is removed from the patient's arm and the cable is disconnected from the wrist-worn processing unit/transceiver 12.

To determine an ECG, the body-worn vital sign monitor 10 features a small-scale, three-lead ECG circuit that collects electrical signals from three chest-worn ECG electrodes. The ECG electrodes are typically disposed in a conventional 'Einthoven's Triangle' configuration which is a triangle-like orientation of the electrodes on the patient's chest that features three unique ECG vectors. From these electrical signals the ECG circuit determines up to three ECG waveforms, which are digitized using an analog-to-digital converter mounted proximal to the ECG circuit, and sent to the wrist-worn processing unit/transceiver 12 according to the CAN protocol. There, the ECG is processed with the PPG to determine the patient's blood pressure.

cNIBP Overview

The cNIBP algorithm is based on the concept of pressure dependent pulse wave velocity. During each cardiac cycle, contraction of the left ventricle creates a pressure pulse wave that travels down the arterial pathways to distal locations. The velocity of the pulse wave is dependent on the volume and stiffness of the artery. This relationship was described by Bramwell and Hill (1922) as given in equation (1).

$$PWV = \sqrt{\left(\frac{V}{\rho}\right)\left(\frac{dP}{dV}\right)} \tag{1}$$

The stiffness of the artery depends on the transmural pressure acting across the arterial wall. This pressure dependence is due to vessel geometry and the viscoelastic properties of vessel wall. Typically the external pressure acting on the wall is negligible and transmural pressure is equivalent to arterial blood pressure. Therefore stiffness and consequently pulse wave velocity are a function of arterial blood pressure. It is the correlation between pulse wave velocity and arterial blood pressure that forms the basis for the cNIBP measurement.

Published literature (Geddes et al., *Psychophysiology* 18: 71-74, 1981; Hughes et al., *Ultrasonic Imaging* 1: 356-367, 1979) suggests that pulse wave velocity correlates best with diastolic and mean arterial pressure (MAP) as given in equation (2).

$$PWV = fcn(MAP) \tag{2}$$

The relationship between pulse wave velocity and mean arterial pressure (MAP) can be accurately captured using a linear model. The relationship between pulse wave velocity and mean arterial pressure is given in equation (3).

$$PWV(t) = a \cdot MAP(t) + pwv_0 \tag{3}$$

The slope (a) and offset ($pwv_0$) in equation (3) are patient specific parameters that require individual calibration.

In order to track the velocity of a patient's pressure pulse the monitoring system measures a parameter known as pulse arrival time (PAT). Every PAT value measured is the sum of two different time intervals, the velocity dependent vascular transit time (VTT) and pre-ejection period (PEP). VTT is the time required by the pressure pulse to travel the arterial pathway. Pre-ejection period is the time interval between the peak of the ECG QRS complex and the opening of the aortic valve. PEP consists of a period of electromechanical delay and a period of isovolumic contraction in the left ventricle. An equation for PAT is given in (4) where the quantity ($L_t$) represents the length of the arterial transit path traveled by the pressure pulse wave.

$$PAT = VTT + PEP = \left(\frac{L_t}{PWV}\right) + PEP \tag{4}$$

Assuming that the monitoring system cannot separate the contribution of PEP from the measured PAT value in order to isolate VTT, PEP is assumed to be constant during the monitoring session. Thus, changes in PAT will be directly attributed to changes in VTT and they will correlate with changes in MAP. In order to derive a relationship between PAT and MAP that maintains the linear relationship between PWV and MAP the expression given in equation (2) is abstracted and defined in terms of the measured PAT value alone as given in equation (5).

$$PAT = \left(\frac{L_t}{PWV}\right) = \left(\frac{L_t}{aMAP + pwv_0}\right) \tag{5}$$

The model parameter values (a) and ($pwv_0$) in this formulation now depend not only on the subject's VTT, but also on their PEP interval at the time of calibration ($PEP_{cal}$). This dependence is shown in equation (6) and (7).

$$pwv_0 = \left(\frac{L_t}{VTT(MAP=0) + PEP_{cal}}\right) \tag{6}$$

$$a = \frac{L_t\left(\frac{VTT_1 - VTT_2}{MAP_2 - MAP_1}\right)}{(VTT_2 + PEP_{cal})(VTT_1 + PEP_{cal})} \tag{7}$$

The expression describing MAP as a function of the measured PAT values can be derived from (5) and is given in equation (8).

$$MAP(t) = \left(\frac{1}{a}\right)\left(\frac{L_t}{PAT(t)} - pwv_0\right) \tag{8}$$

Any error in the PAT estimated MAP that would result from an inaccurate identification of the unknown offset ($pwv_0$) can be eliminated by tracking only the change in PAT and MAP since the time of cuff based calibration. Additionally, this approach also serves to minimize error in the estimated MAP associated with identification of the unknown slope (a) since deviations from the calibrated MAP are likely to be smaller than the overall magnitude of the mean arterial pressure.

Two important parameters measured at the time of calibration are the baseline pulse arrival time ($PAT_{cal}$) and the mean arterial pressure ($MAP_{cal}$). The expression used to calculate mean arterial pressure from the measured PAT values is given in equation (9) where parameter $K=(L_t/a)$. The parameter K, is identified for every patient during inflation of the NIBP cuff.

$$MAP(t) = K \cdot \left(\frac{1}{PAT(t)} - \frac{1}{PAT_{cal}}\right) + MAP_{cal} \tag{9}$$

Systolic (SYS) and diastolic (DIA) arterial pressure are calculated using the mean arterial pressure using the expressions given in equation (10) and (11).

$$SYS(t) = R_{sys} \cdot MAP(t) \tag{10}$$

$$DIA(t) = R_{dia} \cdot MAP(t) \tag{11}$$

Figure 3:
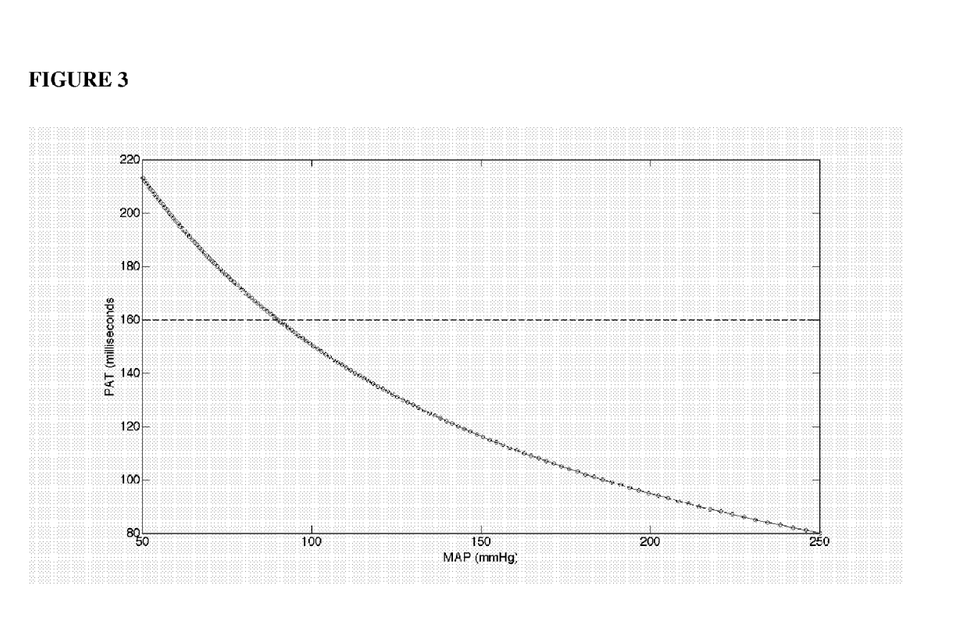
FIG. 3 depicts pulse arrival time as a function of mean arterial pressure ($PAT_{cal}$=160 ms, $MAP_{cal}$=90 mmHg, K=25,600 mmHg*ms).

A range of typical K values are shown in table 1 assuming a linearized slope of 1 mmHg/millisecond at the given baseline PAT. The relationship between pulse arrival time and mean arterial pressure given in (9) is shown graphically in FIG. 3 assuming $MAP_{cal}$=90 mmHg, $PAT_{cal}$=160 ms, and K=25,600 mmHg*ms.

TABLE 1

Equivalence between model parameter K, and a linearized unit slope at various baseline PAT values

| Baseline PAT (ms) | Linearized Slope (mmHg/ms) | K (mmHg * ms) |
|---|---|---|
| 140 | 1 | 19600 |
| 160 | 1 | 25600 |
| 180 | 1 | 32400 |
| 200 | 1 | 40000 |

The cNIBP model parameter values K, $R_{sys}$ and $R_{dia}$ are identified during inflation of the oscillometric cuff. As pressure builds in the NIBP cuff, the duration of the measured pulse arrival time increases. The correlation between cuff pressure and PAT can be produced by several different physiologic mechanisms. Experimental testing and modeling at Sotera Wireless have revealed that the change in compliance of the brachial artery under the cuff is the dominant mechanism causing PAT to increase for cuff pressures below MAP. An increase in cuff pressure ($P_{cuff}$) causes a decrease in the transmural pressure ($P_{tm}$) acting across the arterial wall. As previously described in this document the compliance of the artery is a function of the transmural pressure acting across the wall. An expression for the transmural pressure under the cuff is given in equation (12).

$$P_{tm}(t) = MAP_{cal} - P_{cuff}(t) \quad (12)$$

Figure 2:
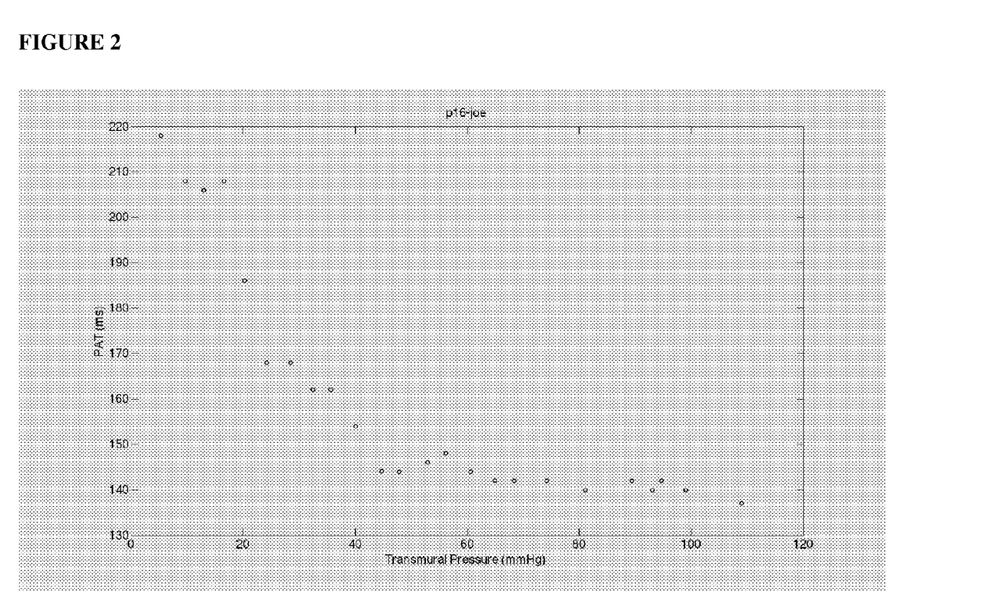
FIG. 2 depicts the relationship between PAT and cuff pressure.

As the transmural pressure acting on the brachial artery decreases with an increase in cuff pressure the pulse wave velocity in this arterial segment decreases. As shown in FIG. 2, a linear model does not accurately characterize the relationship between PAT and transmural pressure. Thus, a nonlinear model is used to describe the relationship between PAT, $MAP_{cal}$, and $P_{cuff}$ during inflation of the NIBP cuff, as given in equation (13) where $L_c$ represents the length of the brachial artery affected by the cuff.

$$PAT(t) = \left(\frac{L_t - L_c}{aMAP_{cal} + pwv_0}\right) + \left(\frac{L_c}{a(MAP_{cal} - P_{cuff}(t)) + pwv_0}\right) \quad (13)$$

The unknown parameter values (a, $K=L_t/a$, and $pwv_0$) are identified from the PAT values and cuff pressures measured during the NIBP inflation period. Additionally, inflation of the NIBP cuff provides an oscillometric blood pressure measurement for systolic pressure ($SYS_{cal}$), diastolic pressure ($DIA_{cal}$), and mean arterial pressure ($MAP_{cal}$).

The ratio used to estimate diastolic pressure ($R_{dia}$) in the cNIBP algorithm is calculated based on the oscillometric blood pressure measurements as given in equation (14).

$$R_{dia} = \left(\frac{DIA_{cal}}{MAP_{cal}}\right) \quad (14)$$

The ratio used to estimate systolic pressure ($R_{sys}$) in the cNIBP algorithm is initially calculated based on the oscillometric blood pressure measurements and is subsequently updated based on the MAP value calculated from the measured PAT values. The expression used to calculate the systolic ratio is given in equation (15).

$$R_{sys} = \left(\frac{SYS_{cal}}{MAP_{cal}}\right) + \overline{m}_{sys}(MAP(t) - MAP_{cal}) \quad (15)$$

Posture and Arm Height Correction

A change in the patient's arm posture (hydrostatic pressure) or a change in their torso posture (cardiac preload) can cause a change in PAT that is unrelated to a change in central blood pressure. If uncorrected these changes in PAT would reduce the accuracy of the cNIBP measurement, trigger false alarms, and cause unnecessary cNIBP calibration alerts. To correct the PAT offset caused by posture, the monitoring system of the present invention combines the torso and arm posture measured by the accelerometers with a real-time system identification algorithm.

Two input variables are used by the cNIBP algorithm to remove PAT offset caused by posture change. One of the variables is the vertical angle of the torso ($\theta_v$), defined as the angle between a vector that is parallel to the superior/inferior axis and the horizontal ground plane. For example a vertical angle of zero degrees would indicate the patient is lying down and a vertical angle of 90 degrees would indicate that the person is standing upright. The second input is a summed or total arm height ($h_t$) variable which is derived from the posture of the upper and lower arm. The vertical angle ($\theta_v(t_{cal})$) and arm height ($h_t(t_{cal})$) of the patient are recorded at the time of the NIBP inflation. All PAT offsets are calculated in relation to these initial postures.

When a significant change in either of these two variables is detected by the monitor, a recursive least squares (RLS) identification algorithm is triggered to identify the PAT offset induced by the posture change. This algorithm was selected because it provides the ability to update and remove offset in real-time on a PAT by PAT basis, does not require storage of data into large arrays, can be implemented using integer mathematics, and the identified slope provides additional insight into the underlying physiology that can be utilized by the algorithm's logic.

The variables used by the RLS algorithm are the change in torso posture since calibration ($\Delta\theta_v$), the change in arm height since calibration ($\Delta h_t$), and the difference between the current PAT and the PAT value measured prior to the posture change ($\Delta PAT$) plus any previously determined PAT offset value as given in equation (16).

$$NewPatOffset(t) = \Delta PAT(t) + PatOffset \quad (16)$$

The RLS algorithm for both torso and arm posture follow the same steps so for brevity the procedure is outlined for arm height only. Given an initial covariance parameter ($P_{old}$) the first step in the RLS algorithm is to update the gain feedback variable ($K_{RLS}$) based on the input variable ($\Delta h_t$) as given in equation (17).

$$K_{RLS} = \frac{P_{old}(\Delta h_t(t))}{1 + P_{old}(\Delta h_t(t))^2} \quad (17)$$

$P_{old}$ determines the rate of convergence for the recursive estimation, and can be assigned an initial value empirically to begin the recursive procedure. A suitable value that can be used is in the range of 0.01-0.04.

The next step in the RLS algorithm is to calculate the unknown model parameter or slope as given in equation (18) based on an initial model parameter ($m_{old}$).

$$m_{RLS} = m_{old} + K_{RLS}(NewPatOffset(t) - m_{old}\Delta h_t(t)) \quad (18)$$

$m_{old}$ represents the slope for arm height and posture, and again can be initialized empirically. Suitable values are −0.2 for arm height (in centimeters) and 0.3 for posture (angle in degrees).

If the updated slope predicts the expected physiologic behavior, e.g. PAT increased when the hydrostatic pressure decreased, then the updated slope is used to calculate the change in PAT caused by hydrostatic pressure or the hydrostatic transit time ($\Delta HTT$) as given in equation (19).

$$\Delta HTT(t) = m_{RLS}\Delta h_t(t) \quad (19)$$

The calculation of the model parameter is a recursive procedure so the covariance and gain feedback parameters are updated prior to the next iteration as given in equation (20), (21), and (22).

$$P = P_{old}\left(1 - \left(\frac{P_{old}(\Delta h_t(t))^2}{1 + P_{old}(\Delta h_t(t))^2}\right)\right) \quad (20)$$

$$P_{old} = P \quad (21)$$

$$m_{old} = m_{RLS} \quad (22)$$

The updated hydrostatic transit time and the change in PAT caused by a change in torso posture ($\Delta PEP(t)$) are subtracted from the measured PAT value ($PAT_{raw}$) prior to calculation of the cNIBP numeric values as given in equation (23).

$$PAT(t) = PAT_{raw}(t) - \Delta HTT(t) - \Delta PEP(t) \quad (23)$$

Following a change in arm or torso posture the RLS algorithm exits the procedure if the model parameters converge to an approximately fixed value or it has run through a specified number of iterations. Upon exiting the algorithm the PAT offset value is updated.

As discussed above, for changes in torso posture the equations are similar:

$$K_{RLS,\theta} = \frac{P_{old,\theta}(\Delta\theta_v(t))}{1 + P_{old,\theta}(\Delta\theta_v(t))^2}$$

$$m_{RLS,\theta} = m_{old,\theta} + K_{RLS,\theta}(NewPatOffset(t) - m_{old,\theta}\Delta\theta_v(t))$$

$$\Delta PEP(t) = m_{RLS,\theta}\Delta\theta_v(t)$$

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. A method of determining patient-specific calibration values for use in a continuous blood pressure measurement based on pulse wave velocity (PWV), the method comprising:

positioning on the patient
(i) a sensor device on a patient, the sensor device configured to measure sensor data indicative of pulse arrival time (PAT) at a first point on an extremity of the patient, the PAT defined as a time difference between ventricular depolarization occurring in a cardiac cycle, and arrival of a pressure wave at the first point resulting from blood flow caused by the ventricular depolarization through a vascular path of length ($L_t$), wherein the sensor device is operably connected to a processing component, and
(ii) an inflatable cuff device on the patient's extremity at a second point on the extremity of the patient at a position on the vascular path between the heart and the first point, the inflatable cuff device comprising an inflatable cuff which is configured to cover a portion of the vascular path of length ($L_c$) and an inflation pump, the inflatable cuff device configured to measure a waveform indicative of cuff pressure on the patient's extremity during inflation, wherein the inflatable cuff device is operably connected to the processing component;

receiving at the processing component the sensor data and the waveform indicative of cuff pressure, and causing the processing component to calculate therefrom a series of pulse arrival times ("PATs") as a function of cuff pressure during inflation of the inflatable cuff to above the patient's systolic blood pressure, wherein the inflation causes a compliance change in the vascular path of length $L_2$, thereby causing the PAT measured by the sensor device to lengthen as cuff pressure is increased; and determining using the processing component one or more coefficients which relate PWV to mean arterial pressure (MAP) by modeling the series of PATs measured as a function of cuff pressure as a nonlinear relationship, wherein the nonlinear relationship is expressed as $$PAT(t) = \left(\frac{L_t - L_c}{aMAP_{cal} + pwv_0}\right) + \left(\frac{L_c}{a(MAP_{cal} - P_{cuff}(t)) + pwv_0}\right)$$

wherein $pWV_0$ is the PWV through the portion of the vascular path covered by the inflatable cuff, and a is a constant.

2. A method according to claim 1, wherein the sensor device comprises (a) an electrical sensor comprising: at least two electrodes configured to detect electrical signals from the patient's body, and an electrical circuit operably connected to the electrodes and configured to process the detected electrical signals, the electrical sensor generating a time dependent electrical waveform indicative of one or more contractile properties of the patient's heart, and (b) an optical sensor comprising a source of electromagnetic radiation configured to irradiate tissue of the patient with radiation emitted therefrom, and a detector configured to detect one or more properties of the electromagnetic radiation after it irradiates soft tissue, the optical sensor generating a time dependent optical waveform indicative of volumetric changes in the irradiated tissue, wherein the sensor data comprises the time dependent electrical waveform and the time dependent optical waveform.

3. A method according to claim 1, further comprising using the processing component to determine a baseline pulse arrival time ($PAT_{cal}$) from the sensor data obtained in the absence of pressure being applied by the inflatable cuff device, and a systolic pressure ($SYS_{cal}$), diastolic pressure ($DIA_{cal}$), and mean arterial pressure ($MAP_{cal}$) from the waveform indicative of cuff pressure on the patient's extremity obtained during inflation.

4. A method according to claim 3, further comprising using the processing component to determine a linear (or non-linear) regression equation between systolic pressure and mean arterial pressure at the time of calibration and a linear (or non-linear) regression equation between diastolic pressure and mean arterial pressure at the time of calibration:

$$DIA_{cal} = R_{dia} * MAP_{cal} + B_{dia}$$

and wherein where the intercept is negligible the ratio $R_{sys}$ and $R_{dia}$ are determined according to the equations:

$$R_{sys} = \left(\frac{SYS_{cal}}{MAP_{cal}}\right)$$

and $$R_{dia} = \left(\frac{DIA_{cal}}{MAP_{cal}}\right).$$

5. A method according to claim 3, further comprising using the processing component to determine a mean arterial pressure at a time t (MAP(t)) subsequent to determining the one or more coefficients which relate PWV to MAP according to the equation $$MAP(t) = K \cdot \left(\frac{1}{PAT(t)} - \frac{1}{PAT_{cal}}\right) + MAP_{cal}$$

wherein K is $L_t/a$.

6. A method according to claim 5, further comprising using the processing component to determine a systolic arterial pressure at a time t (SYS(t)) and a diastolic arterial pressure at a time t (DIA(t)) according to the equations $$SYS(t) = R_{sys} \cdot MAP(t) + B_{sys}$$

and $$DIA(t) = R_{dia} \cdot MAP(t) + B_{dia}$$

* * * * *